Dec. 10, 1957 E. B. LE GRICE Plant Pat. 1,665
ROSA FLORIBUNDA PLANT
Filed Feb. 6, 1957
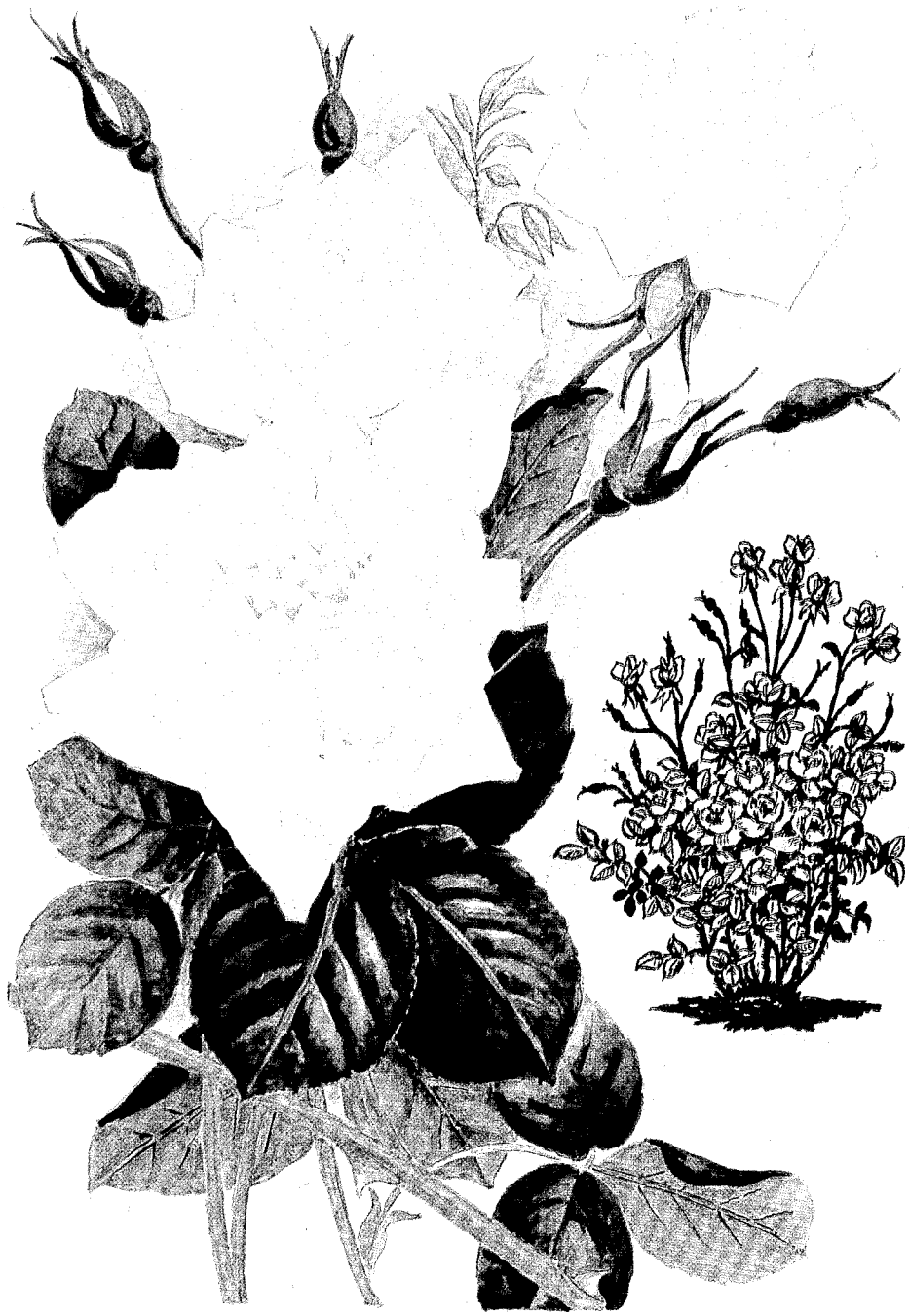
WITNESS
Addison E. Avery
INVENTOR
Edward Burton Le Grice,
by: John Harrout Howard,
ATTY.

United States Patent Office

Plant Pat. 1,665
Patented Dec. 10, 1957

1,665

ROSA FLORIBUNDA PLANT

Edward Burton Le Grice, North Walsham, Norfolk, England

Application February 6, 1957, Serial No. 638,667

1 Claim. (Cl. 47—61)

This invention relates to a new variety of rose plant, a Rosa floribunda hybrid.

The present rose plant was produced originally by crossing a patented Rosa floribunda, known commerially as "Goldilocks," Plant Patent No. 672, as a seed parent, with a patented Rosa hybrid tea, known commercially as "Elinor Le Grice," Plant Patent No. 917, as the pollen parent.

The seed parent "Goldilocks" was produced by a crossing of an unknown seedling with a Rosa floribunda, known commercially as "Dubloons," Plant Patent No. 152.

The pollen parent, "Elinor Le Grice" was originally produced by a crossing of a Rosa hybrid tea, known commercially as "Lillian" with a Rosa hybrid tea, known commercially as "Golden Dawn." Neither Lillian nor Golden Dawn is patented.

Many seedlings from the crossing of the parents were raised one year and about forty all grown in that year, were chosen for further budding testing. The plant of the present application is one of the forty.

The new variety was asexually reproduced by me, at my nurseries at North Walsham, England, by budding. The new variety has been tested in England, Holland and Germany.

The drawing shows in color a number of typical stalks with leaves, buds, blooms and thorns, and in addition a sketch in pen and ink on a reduced scale of a typical bush.

The original seedling has a normally open and much branched root system, the roots being of medium size and from normal to shallow growth with the usual lateral spread. They have not been attacked by diseases. They have a good resistance to wetness and a very good resistance to drought. Their winter resistance protected is good. Unprotected they have withstood up to five degrees below zero Fahrenheit. The root system appears to be very adaptable to different types of soil.

The exposed plant is in the form of a rather dense and compact woody bush of regular contour. It grows generally upright to a height of about 2½ feet, and has a spread of about 2 feet. It grows vigorously, but does not grow tall.

The exposed portion of the plant has a good resistance to low temperature when protected, and has withstood temperatures as low as five degrees below zero Fahrenheit unprotected. Its resistance both to drought and wet seasons is good. It has not been attacked by diseases.

For growth it prefers moderate sun, but is not particular as to exposure. It thrives well in any good garden soil of normal drainage.

Hereinafter, in referencing colors to charts, the charts designated "Plate No. ——" are those from the Maerz and Paul Dictionary of Color, and those designated "Chart No. ——," are from the British Colour Council and Royal Horticultural Society Colour Charts.

The main stalks of the plant are woody and curving and much branched. For this type of plant, they are relatively stiff and tough without being brittle. They are adequate to support the foliage and blooms well.

The new growth of the stalks is a bright green, comparable to Plate 18–L–7, shaded on the exposed side to an oxblood red comparable to Chart 00823.

The old growth is bright green. On the old growth, the color is relatively uniform but on the new growth it is mottled.

The main stalks range from about 2 to 2½ feet in length, and grow divergent upwardly. They have a smooth surface texture. The branches of the main stalks are light green in color and have a smooth surface texture.

The foliage in general is dense, the leaves being alternately arranged and of average quantity. The new leaves on the top surface are bright green, Plate No. 19–L–8, edged and veined with bright brownish-red, such as "Chimney R+" Plate 5–L–10. On the bottom, the new leaves are a dull, lighter green with brown veins.

The old leaves, on the top surface, are green, comparable to Plate 24–L–5 with the mid-rib Chianti Antique Ruby+, Plate 6–L–6, where it joins the petiole. On the bottom, they are dull green comparable to Plate No. 21–K–7, with a yellowish green mid-rib.

In general the color of the old leaves is uniform and that of the new leaves is variegated, the variegation comprising an edging and veining with reddish-brown, almost an oxblood red.

The leaves are of medium size, varying from 3 to 6 inches in length and from 3 to 5 inches in width. They are of the normal shape. On the upper face, they are waxy and glossy. On the lower face, they are smooth. Their persistency on the plant is excellent.

An unusual leaf characteristic is the depth of the color of the green with the deepening red of the mid-rib where it joins the petiole or stem.

The pedicels or leaf stems are of a deep green with a reddish leaf rib in the center. They average in length to about 1 inch and are quite strong. They are heavily fimbriated at the edge, and their surface texture is glossy.

The plant grows and bloows well over a very wide geographical range. It prefers normal good rose plant soil, at temperatures between a maximum of about 75 degrees Fahrenheit and a minimum of about 20 degrees Fahrenheit. It prefers sun, but is otherwise indifferent as to exposure. It is indifferent to wet and dry and hot and cold, seasons, but prefers a well drained, neutral soil. It does best in a rich soil.

The quality of the flowers is somewhat better as conditions approach those preferred. The quantity of the flowers increases with good treatment and soil.

It has shown a wide and unusual adaptability, keeping its color consistently in strong sun and in rain, in cold and heat, and under an unusually wide range of growing conditions. The number of blooms tend to increase somewhat under good growing conditions such as adequate sun and moisture. Larger blooms are produced under cool conditions, but the color is consistent under all of these conditions.

The plant blooms from early June until fall, the blooming being continuous for a period of about six months. Cutting of part of the flowers appears not to change the blooming characteristics or period.

The buds are of medium size, and globular in shape. They are borne upright. Their color, when the sepals first divide, is a straw yellow, Chart No. 604, tipped with red comparable to Plate No. 1–K–4.

When the petals begin to unfurl the color varies from between a straw yellow, Chart No. 604, and Chinese yellow, Chart No. 606. When half blown, the colors are about the same as in the bud when the petals begin to unfurl.

The sepals are long, and at times pointed with fimbricated elongations.

The calyx is normal in shape, and in size is about 3/10 of an inch in diameter. Its surface texture is normal.

The peduncles average from 2 to 4 inches in length and have a smooth surface texture with reddish hairy thorns superimposed. The peduncles generally are green, and relatively strong. The thorns are reddish brown, Plate 55–L–1.

The pedicels average from 2 to 4 inches in length. They have a smooth upper surface with an under surface almost mossy red thorns. Their color generally is a pale green. They are relatively strong.

An increase in the temperature tends to hasten the blooming of the plant.

The blooms average from 3 to 4 inches in diameter and an average plant will bear from 50 to 100 each season. The blooms are borne in cymes. On the plant, they last about fourteen days, and, when cut, about six days.

The petalage ranges from a straw yellow, Chart No. 604 to a Chinese yellow, Chart No. 606. The most outstanding characteristic of the plant is the color of the bloom which is the same throughout the entire bloom, from the outermost petals and innermost petals, from the base to the tips of the petals, and on the upper face and reverse, and throughout the entire extent of the blooming period from the time the bud opens to the time the petals fall.

The general tonality of the plant from a distance, when it is in bloom, is a deep shining golden yellow. There is no noticeable change during the blooming period.

The petals are smooth and broad and wedge shaped, and have the usual imbrications. There are a few petaloids, quite often about six, and of the usual shape.

The fragrance of the blooms is of average strength for floribunda. It is of a quality reminding one of a Calycanthus praecox. The fragrance lasts about six days for cut flowers and from six to eight days for uncut flowers.

The stamens are simple, and in color, Chinese yellow, Chart No. 606. There are about seventy per bloom. The filaments are of medium size, being about 3/10 of an inch in length, and, in color, Chinese yellow. The pollen likewise is Chinese yellow, as are the styles and stigmas.

The styles are about 2/10 of an inch in length. The stigmas are about 1 mm. wide and plentiful.

The fruit is of the usual form and abundance. At maturity it is green.

On the main stalk, from the base of the plant, the thorns are moderate. On the laterals from the main stalk, they are few. Generally the thorns are in the form of prickles which are relatively long and hooked and quite stiff. In color they are an oxblood red. They are unevenly distributed on the main stalk and on the laterals. On the peduncles many are almost mossy.

The drawing further illustrates the charactertics of the variety and the following tabulation is a detailed description of the new variety:

*General*

Parentage:

*Seed parent.*—"Goldilocks," Plant Patent No. 672, resulting from a cross between an unknown seedling and "Dubloons," Plant Patent No. 152.

*Pollen parent.*—"Elinor Le Grice," Plant Pat. No. 914, a cross between "Lillian" and "Golden Dawn," both of which latter roses are unpatented.

Classification:

*Botanic.*—Rosa floribunda hybrid.

*Flower*

Blooming habit:

*Location where observations were made.*—Roseland Nurseries, North Walsham, England; National Rose Trial Grounds, England; National Test Garden, Holland; test fields at Spearrieshoop, Germany. (This plant was the winner, for 1956, of the Award of Merit of the Royal Horticultural Society at the Chelsea, England, Flower Show, and of the Gold Medal of the National Rose Society of England.)

*Flowering.*—Continuous for about six months from early June until frost.

Bud:

*Size.*—Medium.

*Form.*—Globular.

*Color.*—When sepals first divide, petals are straw yellow tipped with red; when petals begin to unfurl and when half blown, between a straw yellow, Chart No. 604 and Chinese yellow, Chart 606.

*Sepals.*—Long and pointed, sometimes with fimbriated elongations, somewhat recurvent at tips, and light green in color.

*Calyx.*—Shape—usual. Size—about 3/10 of an inch in diameter. Aspect—usual.

*Peduncle.*—Length—from two to four inches. Aspect—smooth with reddish hairy thorns superimposed. Color—green. Strength—strong.

*Opening.*—Normal, hastened by hot conditions.

Bloom:

*Size.*—Three to four inches in diameter.

*Borne.*—In cymes.

*Stems.*—Length two to four inches; strong. Aspect—smooth under surface with almost mossy. Color—bright green with red veins.

*Form.*—When first opened—usual.

*Permanence.*—On the plant—about 14 days. When cut—about six days.

Petalage:

*Number of petals under normal conditions.*—Normal.

*Color.*—Between a straw yellow, Chart 604, and Chinese yellow, Chart 606.

*Variegations.*—The color is the same throughout the petals from base to tip, inside and reverse, and from center of flower to periphery, and from the early opening of the bud until the falling of the petals, this being the most distinguishing feature of the plant.

*Discoloration.*—None.

Petals:

*Texture.*—Smooth.

*Appearance.*—Clear and intense yellow, both inside and reverse, straw yellow, Chart 604 to Chinese yellow, Chart 606.

*Form.*—Broad, wedge shaped.

*Arrangement.*—Usual imbrication.

*Petaloids in center.*—Few, about six.

*Persistence.*—Good.

*Fragrance.*—Average for floribunda, with a quality similar to that of Calycanthus praecox.

*Lasting quality.*—On plant—6 to 8 days. When cut—6 days.

Genital organs:

*Stamens.*—Simple.

*Color.*—Chinese yellow, Chart 606.

*Arrangement.*—Regular and abundant, about 70 per bloom.

*Filaments.*—Medium.

*Color.*—Chinese yellow.

*Pollen.*—Chinese yellow.

*Styles.*—2/10 of an inch, colored Chinese yellow.

*Stigmas.*—About 1 mm. wide.

*Color.*—Chinese yellow.

*Ovaries.*—Plentiful.

Fruit:

*Variety and form.*—Usual.

*Color and maturity.*—Green.

*Plant*

Form: A woody bush, generally upright, dense and compact, regular contour.

Growth: Vigorous but not high, about 2½ feet high, 2 foot spread.

Foliage: Dense.

*Size.*—Medium length from 3 to 6 inches and width from 3 to 5 inches.

*Quantity.*—Average.

*Color.*—New leaves, on top, bright green, Plate No. 19–L–8, edged and veined with bright brown red, almost an oxblood red or Chimney R+, Plate No. 5–L–10. Old leaves can be described as shiny olive green, Plate No. 24–L–5, with a red midrib, Plate No. 6–L–6; on their under side, old leaves dull green with a yellowish green mid-rib, Plate No. 21–K–7.

*Shape.*—Normal.

*Texture.*—Upper side waxy and glossy; lower face smooth; average thickness, borne alternately.

*Edge.*—Serrated, color reddish, Plate No. 6–L–6.

Petiole: Length, about 1 inch, with glossy texture; heavily fimbriated at the edge. Color—deep green with a reddish rib in the center.

Stipules: Light green.

Wood:

*Newest wood.* — Color — bright green Plate No. 18–L–7, red on the exposed side, Chart No. 00823.

*Bark.*—Smooth.

*Old wood.*—Color—bright green.

*Bark.*—Smooth.

Thorns:

*Quantity.*—Moderate on main stalks from base, few on laterals.

*Form.*—Large, long and hooked, stiff.

*Color.*—Reddish brown, Plate No. 55–L–1.

*Position.*—Unevenly distributed on main stalks and laterals and peduncles many, almost mossy.

The most distinctive feaure and charactristic of the new hybrid rose plant is the yellow color of the blooms and its intensity and consistency in all stages of bloom, throughout the entire blooming period, and all parts of the flower. Other distinctive features are the depth of color of the foliage and the deepening red of the mid-rib where it joins the petiole and stem; the bearing of the flowers, many of which are carried singly, but quite often in flower heads springing from the base; the production on side shoots of from one to three flowers, the excellent health of the plant, and its medium bushy growth which makes it excellent for bedding.

Having shown and described my new variety of Rosa floribunda plant, and its manner of asexual reproduction, I claim:

The new and distinct variety of Rosa floribunda plant herein shown and described.

No references cited.